United States Patent [19]

Fujii et al.

[11] Patent Number: 5,328,678
[45] Date of Patent: Jul. 12, 1994

[54] COMPOSITION AND METHOD OF USE FOR LIPOSOME ENCAPSULATED COMPOUNDS FOR NEUTRON CAPTURE TUMOR THERAPY

[75] Inventors: Gary Fujii, Torrance; Paul G. Schmidt, San Marino; Ronald C. Gamble, Altadena, all of Calif.

[73] Assignee: Vestar, Inc., San Dimas, Calif.

[21] Appl. No.: 998,886

[22] Filed: Dec. 28, 1992

Related U.S. Application Data

[63] Continuation of Ser. No. 414,589, Sep. 26, 1989, abandoned, which is a continuation of Ser. No. 116,764, Nov. 4, 1987, abandoned.

[51] Int. Cl.$^5$ .................... A61K 43/00; A61K 9/133
[52] U.S. Cl. .................... 424/1.21; 424/450
[58] Field of Search .................... 424/1.1, 450

[56] References Cited

U.S. PATENT DOCUMENTS

| | | | |
|---|---|---|---|
| 4,086,330 | 4/1978 | Petkau et al. | 424/1.1 |
| 4,399,817 | 8/1983 | Benedict | 424/1.1 X |
| 4,466,952 | 8/1984 | Hadd | 424/1.1 |
| 4,588,578 | 5/1986 | Fountain et al. | 424/1.1 |
| 4,674,480 | 6/1987 | Lemelson | 424/1.1 X |
| 5,019,369 | 5/1991 | Presant et al. | 424/1.1 |

OTHER PUBLICATIONS

Goldenburg, D. M. et al., Neutron–capture therapy of human cancer . . . , *PNAS*, 81:560–63 (1984).
Hatanaka et al., "A Revised Boron–Neutron Capture Therapy", *Z. Neurol*, 204, (1973), pp. 309–332.

*Primary Examiner*—Robert L. Stoll
*Assistant Examiner*—John M. Covert
*Attorney, Agent, or Firm*—Lyon & Lyon

[57] ABSTRACT

Liposomes with hyperosmotic concentration of compounds encapsulated therein are targeted to tumors for neutron capture therapy. The compounds have an element with a large neutron capture cross section and an isotope that emits alpha particles when bombarded with neutrons. A method employing such liposomes for neutron capture therapy is also described.

16 Claims, No Drawings

COMPOSITION AND METHOD OF USE FOR LIPOSOME ENCAPSULATED COMPOUNDS FOR NEUTRON CAPTURE TUMOR THERAPY

This is a continuation of co-pending application Ser. No. 07/414,589, filed on Sep. 26, 1989, now abandoned which is a continuation of co-pending application Ser. No. 07/116,764 filed on Nov. 4, 1987, now abandoned.

FIELD OF THE INVENTION

This invention generally relates to a composition and method for treating tumors, and more particularly to a composition and method of treating tumors using liposome encapsulated compounds in neutron capture therapy.

BACKGROUND OF THE INVENTION

Neutron capture therapy is an attractive method for cancer therapy, specifically the treatment of malignant tumors. The generalized reaction involves capture of a thermalized neutron (usually from a nuclear reactor with special moderators and ports) by an appropriate nucleus having a large neutron capture cross section. The subsequent decay emits energetic particles (alpha particles) which can kill nearby tumor cells. Boron-10, for example, has such an appropriate nucleus and has particularly advantageous properties for this scheme. The boron-10/thermal neutron capture reaction is (asterisk indicating an unstable intermediate state of the Boron nucleus):

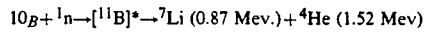

$$^{10}B + ^{1}n \rightarrow [^{11}B]^* \rightarrow ^{7}Li\ (0.87\ \text{Mev.}) + ^{4}He\ (1.52\ \text{Mev})$$

In order for this therapy to be effective, sufficient $^{10}B$ must be localized in a tumor to generate the required density of particles. This level has been variously estimated to be approximately 10-50 ug$^{10}$B/gm tumor. Furthermore, the concentration of $^{10}B$ in normal tissue and blood should be limited and preferably less than the concentration in tumor in order to minimize damage to healthy cells and blood vessels. H. Hatanaka (1986) Boron-Neutron Capture Therapy for Tumors; Nishimura Co., Ltd. p. 1-16.

Large numbers of boron-containing compounds have been tested for their ability to satisfy the above criteria. With few exceptions all have failed as not enough boron has localized in the tumor and the concentration in the blood has been too high for effective neutron capture therapy. Human clinical trials with $Na_2B_{12}H_{11}SH$ in Japan have shown some promise, but only for a limited group of brain tumors. (gliomas) Id. 16-26.

Neutron capture therapy would be greatly expanded in usefulness if a generalized method for delivering high concentrations of $^{10}B$ to tumors were available. It would further be useful if more $^{10}B$ collected in tumor than in the blood. Recently, it has become possible to deliver drugs and other compounds selectively to tumors using liposomes of a particular composition and structure. See, for example, co-pending Vestar, Inc. patent application Ser. No. 674,201 entitled "Method of Targeting Tumors in Humans" which is incorporated herein by reference and which describes incorporation of radioactive agents at levels a million fold less than what is required for successful neutron capture therapy. Incorporation of compounds with higher osmolarity inside liposomes than outside, as is necessary for effective neutron capture therapy, has heretofore never been achieved and has been considered to be an unstable condition since the extra osmotic pressure should lead to breakage of the liposomes and/or leakage of the contents. Successful neutron capture therapy with liposomes depends on incorporating the highest concentration of $^{10}B$ possible without substantially altering the liposome's favorable biodistribution characteristics. That can be accomplished by using compounds with the highest number of boron atoms practicable and by incorporating boron into liposomes at the highest possible concentration consistent with liposomes that are stable and target to tumors. It was found in the present invention that hyperosmotic solutions could be stably encapsulated while still maintaining good animal biodistribution performance. Thus the objective of at least 10 ug $^{10}$B per gram of tumor tissue could be met (assuming use of >90% $^{10}$B enriched material). The present invention thus offers a method employing specially formulated liposomes, which encapsulate unexpectedly high concentrations of boron-containing compounds, and which collect in tumor tissue after intravenous injection or direct infusion into the artery that supplies the tumor. After a time to enable sufficient accumulation of boron-containing compounds in the tumor tissue, the subject can be subjected to a source that emits neutrons effective for neutron capture therapy.

SUMMARY OF INVENTION

It is an object of the invention to provide a method for delivering therapeutically useful concentrations of boron-containing compounds to tumors for use in neutron capture tumor therapy.

It is a further object to provide a liposome formulation, encapsulating boron-containing compounds, that has the properties of retaining concentrations of said boron compounds inside the liposomes without significant breakage.

It is a further object of the invention to provide a method for cancer therapy through use of liposomal encapsulated boron-containing compounds, the means to deliver at least 10 micrograms $^{10}$B per gram of tumor tissue to animal and human tumors, while minimizing the concentration in the blood.

DETAILED DESCRIPTION OF THE INVENTION

Liposomes are microscopic structures consisting in part of phospholipids. Methods for forming these liposomes are, by now, well known in the art and any such methods can be employed in the context of the present invention. Phospholipids are composed of 2 fatty acid chains condensed with glycerol with an additional substitution of a phosphate ester head group. We have found that by incorporating certain phospholipid molecules, a liposome is obtained which is stable in vivo. It is known that phase transition points are a function of hydrocarbon chain length, C. Lanford, *The Hydrophobic Effect*, 2d Ed (1980). Certain phospholipid molecules exhibit phase transitions at relatively high temperatures (greater than 37° C.) and we have found that use of these phospholipids in the compositions described herein provide liposomes with improved stability in vivo. When hydrated, phospholipids form into bilayer structures with their fatty acid hydrocarbon tails pointed inward and the polar head groups outward. A hydrated phospholipid suspension, when agitated, forms multilamellar vesicles (MLV) like tiny onions, with water separating many bilayers. Application of a shearing force such as sonication to an MLV suspension produces small single bilayer vesicles (SUV) of a size range generally 30–200 nm in average diameter. Other lipids may be combined with phospholipids to produce liposomes having particular properties. Specifically sterols such as cholesterol help stabilize the bilayer toward leakage and destruction in blood plasma. A stable liposome may be obtained by incorporating 5–50% cholesterol by weight of phospholipid into the liposome. Charged lipids or lipids with specific ligand functions may also be included.

SUV comprised of distearoylphosphatidylcholine (DSPC) and cholesterol are particularly advantageous for delivery of radioactive compounds to tumors.

There are non-radioactive isotopes other than boron-10 that do show a large capture cross-section for thermal neutrons suitable for the present invention, namely: $^3$He $^{149}$Sm, $^{235}$U, $^6$Li, $^{113}$Cd, $^{155,157}$Gd. Except for lithium and uranium however, the other listed elements produce gamma radiation after absorbing a thermal neutron. The resulting gamma rays are not confined to the target cells, and therefore are less desirable for use with the present invention, although certainly capable of being used therein.

Boron compounds to be used can have two or more atoms of boron per molecule, but preferably contain at least 10 atoms of boron per molecule. The isotopic content of the boron can range from natural abundance 19.78% $^{10}$B to greater than 95% $^{10}$B for a highly enriched compound. Natural abundance material is useful for test studies of encapsulation, biodistribution, stability and the like. Highly enriched material is advantageous for therapy where the maximum practicable concentration of $^{10}$B is required.

Preferable boron-containing compounds are highly water soluble, have small or no charge at physiological pH, are relatively impermeable to phospholipid bilayers of liposomes, and are not toxic or have low toxicity to the therapy subject. Examples are $Na_2B_{10}H_{10}$, $Na_2B_{12}H_{12}$, $Na_2B_{12}H_{11}SH$, and $Na_2B_{10}O_{16}$. A concentration of at least 250 mM inside of the liposome is necessary for a boron compound having at least 10 boron atoms per molecule. Of course, with a lower amount of boron atoms per molecule, a higher concentration is required.

In one preferred embodiment liposomes are prepared from a mixture of DSPC and cholesterol (1:1 molar ratio). The dried lipid film is hydrated with an aqueous solution of $Na_2B_{10}H_{10}$. Shear force is applied to the solution by sonication or other suitable homogenizing technique to produce small unilamellar vesicles (SUV) whose average diameter is less than 200 nm and preferably 30–100 nm. The non-encapsulated $Na_2B_{10}H_{10}$ is separated from the liposomes by gel filtration chromatography using a Sephadex G-25-80 column equilibrated with phosphate buffered normal saline, or with lactose at an osmolarity approximately equal to physiological. The resulting liposome solution is stable to leakage of the material inside, such that less than 10% of the boron material leaks out over a period of 3.5 months (Tables 2 and 3).

The cholesterol-DSPC liposomes with 250 mM $Na_2B_{10}H_{10}$ and $^{111}$In-EDTA as a radioactive tracer inside are injected into the tail vein of Balb/c mice. The animals have previously been implanted subcutaneously with EMT6 tumor cells in the right flank. At various time points the animals are sacrificed and their blood, tumor, liver and spleen are tested for concentrations of the $^{111}$In compound by measuring gamma radiation levels. Insofar as the In-EDTA complex behaves like $B_{10}H_{10}{}^{2-}$, the radioactive tracer represents the biodistribution of the boron compound. The results show that boron −10 can be delivered to tumors at levels sufficient to give therapeutic value in neutron capture therapy.

The invention extends to other boron compounds where the number of boron atoms per molecule is at least two, preferably 10 and to polymeric boron compounds so as to maximize the boron concentration inside the liposome. The invention includes the methods of performing neutron capture tumor therapy by administering boron-containing liposomes and thereafter, subjecting the patient to a source that emits neutrons. Such a source was described for example in U.S. Pat. No. 4,516,535 issued to Russell, Jr. et al.

Preparation of $Na_2B_{10}H_{10}$, in water (normal isotopic abundance)

The $Na_2B_{10}H_{10}$ was prepared from the bis-triethylammonium salt of $B_{10}H_{10}=$ by methods well known in the art.

The bis-triethylammonium salt of $B_{10}H_{10}=$ was synthesized by the procedure set forth in Hawthorne, M. F.; Pilling, R. L., *Inorg. Syn,* 1967, 9, 16, incorporated herein by reference.

Preparation Of Liposome Encapsulated $Na_2B_{10}H_{10}$

To a 15 ml glass tube was added 166 mg DSPC (Avanti Polar Lipids, Birmingham, Ala.) and 84 mg cholesterol (Calbiochem, San Diego, Calif.) (molar ratio 1:1) in 5.0 ml $CHCl_3$/menthanol (75:25 v/v). The solution was evaporated with a stream of nitrogen to form a film on the inside of the tube. The tube was placed under vacuum for at least 12 hours. To this tube was added 5.0 ml of a 250 mM solution of $Na_2B_{10}H_{10}$ in distilled water. The osmolarity of the 250 mM $Na_2B_{10}H_{10}$ solution was separately measured using an osmometer (model OW2, Advanced Instruments, Needham Heights, Mass.) and found to be 730 mOsm/lit. The hydrated lipid sample was sonicated using a Sonics and Materials Vibracell probe sonicator with a microtip operated at the maximum power setting for the microtip. The solution was maintained at 65° C. and under $N_2$ atmosphere and sonicated for 15 minutes. The sample was then allowed to cool to room temperature. The process was repeated for a second sample.

The processed liposome samples were separately applied to Sephadex G-25-80 columns (10 × 1 cm) equilibrated with 5 mM phosphate pH 7.5 in 0.9% saline (PBS) or 90 mg/ml lactose. Both of these solutions in the columns were at 295 mOsm/lit osmolarity. The liposomes were eluted by vacuum, in the process exchanging their outside $Na_2B_{10}H_{10}$ for PBS or lactose. The liposome containing fraction was collected from the column.

Size Analysis of Liposome Encapsulated $Na_2B_{10}H_{10}$

The size of the liposomes was determined by dynamic light scattering using a Nicomp model 270 laser light scattering unit. A volume of 20 microliters of the sample were diluted into 750 microliters phosphate buffered saline (PBS) for the measurement. Results for the Gaussian distribution mode are shown below in Table 1.

TABLE 1

| Sample Stored in | Mean Diameter (volume weighed) |
| --- | --- |
| PBS | 69.8 nm |
| Lactose | 75.3 nm |

Encapsulated Concentration of $Na_2B_{10}H_{10}$

The encapsulated concentration of $Na_2B_{10}H_{10}$ was gauged by measuring the total decahydrodecaborate concentration by a colorimetric method in each sample and then in the effluent after ultrafiltration to correct for material outside the liposomes. The colorimetric method is described in Hawthorne, M. F., Olsen, F. P. J.Am. Chem. Soc., 1965, 87, 2366, which is incorporated herein by reference.

This colorimetric method depends upon the rapid and quantitative formation of an intensely colored blue azo dye ($\lambda_{max}$ 5200 Å $\epsilon = 2 \times 10^4$) produced by coupling benzene diazonium ion with the 1-position of the $B_{10}H_{10}^{2-}$ ion in acetonitrile solution in the presence of trifluoroacetic acid. This method can quantitatively determine $B_{10}H_{10}^{2-}$ at concentrations as low as $1 \times 10^{-5}$M. The results are shown below in Table 2.

TABLE 2

| Liposome Sample in | $Na_2B_{10}H_{10}$ (mM) | | |
| --- | --- | --- | --- |
| | Total | Outside | Inside |
| PBS | 4.8 | 0.35 | 4.45 |
| Lactose | 3.5 | 0.18 | 3.32 |

Very little of the decahydrodecaborate is outside the liposome initially (5-8%).

Encapsulated Concentration of $Na_2B_{10}H_{10}$ (after 3.5 months)

The samples were stored at room temperature (21°-23° C.) for 3.5 months and then retested.

TABLE 3

| Liposome Sample in | $Na_2B_{10}H_{10}$ (mM) | | |
| --- | --- | --- | --- |
| | Total | Outside | Inside |
| PBS | 4.8 | 0.63 | 4.17 |
| Lactose | 3.5 | 0.11 | 3.39 |

After 3.5 months the liposomes stored in PBS have leaked only about 6% more boron compound from the inside to outside, while those stored in lactose have lost no boron within the experimental error of the measurement. Thus the liposomes of the invention can maintain for months a solution of 730 mOsm/lit. decahydrodecaborate inside while the outside solution is only 295 mOsm/lit.

Biodistribution of Boron encapsulated Liposomes in Mice Using an $^{111}$In chelate liposome label Liposome samples were prepared as discussed above except that the ionophore A23187 was included in the lipid at a level of $10^{-3}$ of the weight of the phospholipid. The hydrating solution [2.5 ml] was 250 mM M $Na_2B_{10}H_{10}$ and 1 mM EDTA. The outside solution of the sonicated liposomes was exchanged for PBS by vacuum elution from Sephadex G-25-80 as before. These liposomes had a mean diameter of 57.9 nm. Lipid analysis showed 14.3 mg/ml DSPC and 7.67 mg/ml cholesterol. A sample of the exchanged liposomes was incubated with 50 ul radioactive $^{111}$InCl$_3$ and 5 mM sodium citrate at 80° C. for 30 minutes. $^{111}$In$^{+3}$ is transported by A23187 to the EDTA inside the liposome in this procedure. Tests of In concentration in the total sample and outside after loading showed a loading efficiency of 93%, that is, 93% of the added $^{111}$In was inside the liposomes as the In-EDTA complex. A similar preparation using the ultrafiltration step and colorimetric assay for $Na_2B_{10}H_{10}$, showed that less than 1% of the $Na_2B_{10}H_{10}$ had leaked out of the liposomes during the 30 min. incubation at 80°.

$^{111}$In chelated to EDTA is used as a radioactive tracer in this experiment since direct measurement of the $B_{10}H_{10}^{-2}$ species in animal tissues proved to be impossible by known methods. The In-EDTA complex is exceedingly stable so that the radioactive ion does not dissociate to any appreciable extent in the body. The complex is negatively charged and highly water soluble as is the $B_{10}H_{10}^{-2}$ ion. Thus the In-EDTA and $B_{10}H_{10}^{-2}$ are expected to have very similar pharmacokinetics in mouse biodisdribution studies. Therefore, the percent injected dose per gram tissue measured from the radioactivity of $^{111}$In gamma emission should correspond closely to the distribution of $B_{10}H_{10}^{-2}$.

The $^{111}$In-EDTA loaded liposomes still containing 250 mM $Na_2B_{10}H_{10}$ (inside concentration) were injected into the tail vein of Balb/c mice having an 8 day old implanted EMT6 tumor in the flank. A volume of 200 microliters of the liposome sample was injected in each mouse. Mice were sacrificed in groups of 5 at 24, 48, and 72 hours after injection. Tissues were dissected, weighed and analyzed for radioactivity in a gamma counter. The results, expressed as the average percent $^{111}$In injected dose per gram (% ID/gram) tissue are listed below:

TABLE 4

| Tissue | Time Post Injection (hrs) | | |
| --- | --- | --- | --- |
| | 24 | 48 | 72 |
| Blood | 7.8 | 0.5 | 0.08 |
| Tumor | 10.3 | 3.8 | 2.2 |
| Liver | 11.4 | 3.8 | 2.3 |
| Spleen | 14.7 | 7.9 | 6.4 |

At 24 hours the tumor level is greater than the blood, optimal for neutron capture therapy.

As set forth in Table 4, after 24 hours the In uptake in the tumor is 10.3% injected dose per gram (ID/gram). We can therefore estimate the amount of $10_B$ deliverable to a tumor at the 24 hour level as likewise 10.3% injected dose per gram. The injected dose was 200 microliters of a liposome sample of 21.97 mg/ml lipid concentration. Liposomes of the kind used here encapsulate at least 1.0 microliter of solution per mg. lipid. That means 21.97 microliters or 2.2% are entrapped per ml of solution in the sample used. The injected dose of 100 microliters contained 0.2 ml $\times 0.022 \times 250$ micromoles/ml $B_{10}H_{10}^{-2}$ or 1.10 micromoles $B_{10}H_{10}^{-2}$. If the isotopic enrichment were 90% $^{10}$B or greater, the total $^{10}$B injected would be 1.10 micromoles $\times$ 90 micrograms $^{10}$B micromole $B_{10}H_{10}^{2-} = 99.0$ micrograms $^{10}$B. For a tumor level of 10.3% ID/gm the tumor concentration would then be 10.2 micrograms $^{10}$B per gram tumor which is within the range considered to be necessary for successful neutron capture therapy.

Although this invention has been described with reference to particular applications, the principles involved are susceptible of other applications which will be apparent to those skilled in the art. The invention is accordingly to be limited only by the scope of the appended claims.

We claim:

1. Neutron capture therapy agents to deliver a compound to a tumor, comprising small unilamellar liposomes having an average diameter of from about 30 to about 200 nm, said liposomes encapsulating a compound at a concentration of greater than 250 mM, said compound containing an element which has a large neutron cross-section and is capable of forming an isotope which emits an alpha particle from within said liposomes when bombarded with neutrons, which liposomes are stable against leakage and destruction.

2. The therapy agents of claim 1 wherein said liposomes are comprised of phospholipids having a phase transition temperature greater than 37° C.

3. The therapy agents of claim 2 wherein said phospholipid is distearoyl phosphatidylcholine.

4. The therapy agents of claim 1 wherein said compound is a boron compound.

5. The therapy agents of claim 4 wherein said boron compound contains at least 10 atoms of boron per molecule.

6. The therapy agents of claim 4 wherein said boron compound is selected from the group consisting of $Na_2B_{10}H_{10}$, $Na_2B_{12}H_{12}$, $Na_2B_{12}H_{11}SH$, or $Na_2B_{10}O_{16}$.

7. The therapy agents of claim 1 wherein said compound contains the elements $^{10}B$, $^{235}U$, or $^{6}Li$.

8. A method of neutron capture therapy treatment of a tumor comprising introducing into the bloodstream of a subject neutron capture therapy agents comprising small unilamellar liposomes having an average diameter of from about 30 to 200 nm, said liposomes encapsulating a compound at a concentration of greater than 250 mM, said compound containing an element
   (a) having a large neutron capture cross-section, and
   (b) being capable of forming an isotope which emits an alpha particle from within said liposomes when bombarded with neutrons, which liposomes are stable against leakage and destruction,
and after a time to enable sufficient accumulation of said isotope in the tumor tissue, subjecting the subject to a source that emits neutrons effective for neutron capture therapy.

9. The method of claim 8 wherein said compound is a boron compound.

10. The method of claim 9 wherein said boron compound is water soluble, has little or no charge at physiological pH, and has no or little toxicity to the subject.

11. Them method of claim 9 wherein said boron compound is encapsulated in a concentration sufficient to accumulate said isotope in the tumor at a concentration of about 10 µg/g to about 50 µg/g tumor.

12. The method of claim 8 wherein said liposomes are comprised of phospholipids having a phase transition temperature greater than 37° C.

13. The method of claim 12 wherein said phospholipid is distearoyl phosphatidylcholine.

14. The method of claim 9 wherein said boron compound contains at least 10 atoms of boron per molecule.

15. The method of claim 9 wherein said boron compound is selected from the group consisting of $Na_2B_{10}H_{10}$, $Na_2B_{12}H_{12}$, $Na_2B_{12}H_{11}SH$, or $Na_2B_{10}O_{16}$.

16. The method of claim 8 wherein said compound contains the elements $^{10}B$, $^{235}U$, $^{6}Li$.

* * * * *

UNITED STATES PATENT AND TRADEMARK OFFICE
Certificate

Patent No. 5,328,678

Patented: July 12, 1994

On motion pursuant to 37 CFR § 1.634 in Interference No. 103,855, it has been found that the above-identified patent, through error and without any deceptive intention, incorrectly sets forth the inventorship.

Accordingly, pursuant to 35 U.S.C. § 256, it is hereby certified that the correct inventorship of this patent is: Gary Fujii, Paul G. Schmidt, Ronald C. Gamble and M. Frederick Hawthorne.

Signed and Sealed this Second Day of June, 1998.

MARY F. DOWNEY
*Administrative Patent Judge*
Board of Patent Appeals and Interference